(12) United States Patent
Walneck et al.

(10) Patent No.: US 7,014,639 B2
(45) Date of Patent: Mar. 21, 2006

(54) APPARATUS FOR AESTHETIC SKIN TREATMENTS

(75) Inventors: Charles T. Walneck, Cary, IL (US); Tami L. Brennan-McClure, Cary, IL (US); James H. Santee, Cary, IL (US)

(73) Assignee: SkinCare Technology, Inc., Hernando Beach, FL (US)

( * ) Notice: Subject to any disclaimer, the term of this patent is extended or adjusted under 35 U.S.C. 154(b) by 191 days.

(21) Appl. No.: 10/374,564

(22) Filed: Feb. 25, 2003

(65) Prior Publication Data

US 2004/0167497 A1 Aug. 26, 2004

(51) Int. Cl.
*A61B 18/18* (2006.01)

(52) U.S. Cl. .................. 606/9; 606/3; 606/10; 606/11; 607/88; 607/89; 607/91

(58) Field of Classification Search ............ 606/1, 606/3, 9–12, 27–31, 131; 607/88, 91, 93, 607/96, 100; 362/551–556, 583
See application file for complete search history.

(56) References Cited

U.S. PATENT DOCUMENTS

| | | | |
|---|---|---|---|
| 4,232,678 A | * | 11/1980 | Skovajsa ................... 607/89 |
| 4,787,373 A | | 11/1988 | Vogel |
| 4,930,504 A | * | 6/1990 | Diamantopoulos et al. ... 607/88 |
| 5,259,380 A | * | 11/1993 | Mendes et al. ............. 607/115 |
| 5,551,949 A | | 9/1996 | Kim |
| 5,660,836 A | | 8/1997 | Knowlton |
| 5,755,752 A | * | 5/1998 | Segal ........................ 607/89 |
| 6,009,876 A | | 1/2000 | Yavitz |
| 6,019,482 A | | 2/2000 | Everett |
| 6,030,374 A | | 2/2000 | McDaniel |
| 6,053,906 A | * | 4/2000 | Honda et al. ............... 606/1 |
| 6,120,497 A | | 9/2000 | Anderson |
| 6,149,644 A | | 11/2000 | Xie |
| 6,264,652 B1 | | 7/2001 | Eggers |
| 6,283,956 B1 | | 9/2001 | McDaniel |
| 6,309,387 B1 | | 10/2001 | Eggers |
| 6,312,397 B1 | | 11/2001 | Gebhard |
| 6,312,450 B1 | | 11/2001 | Yavitz |
| 6,398,753 B1 | | 6/2002 | McDaniel |
| 6,443,915 B1 | | 9/2002 | Hwang |
| 6,569,109 B1 | * | 5/2003 | Sakurai et al. ............. 601/2 |
| 6,629,971 B1 | | 10/2003 | McDaniel |
| 6,663,659 B1 | | 12/2003 | McDaniel |
| 6,676,655 B1 | | 1/2004 | McDaniel |
| 6,702,837 B1 | * | 3/2004 | Gutwein ..................... 607/88 |

* cited by examiner

*Primary Examiner*—A. Farah
(74) *Attorney, Agent, or Firm*—Bell, Boyd & Lloyd LLC

(57) ABSTRACT

An apparatus for aesthetic manipulation of the skin having a large pulsator with plurality of light emitting diodes of at least two different wavelengths and a small pulsator with one light emitting diode is disclosed. A frequency modulator automatically modulates the emitting frequency of the tight emitting diodes to a plurality of different frequencies. A power output modulator is provided to modulate the power output of the light emitting diodes. A phase switching subsystem allows selection between a plurality of operating phases, each operating phase operating the frequency modulator and power output modulator in a different predetermined manner. Calibration subsystem connected in circuit with the light emitting diodes calibrates the power output of the light emitting diodes. A vibrator is provided to vibrate the large pulsator. A vibration switching subsystem selectively activates the vibrator.

17 Claims, 5 Drawing Sheets

APPARATUS FOR AESTHETIC SKIN TREATMENTS

BACKGROUND OF THE INVENTION

1. Field of the Invention

The claimed invention generally relates to devices for aesthetic manipulation of the skin. More specifically, the claimed invention relates to a method and apparatus for aesthetic manipulation of the skin accomplished by modulation of the frequency, wavelength and output of light emitting diodes.

2. Description of the Prior Art

As segments of the population, such as the "baby boomer" generation, get older, the market for products that help reduce the signs of aging has drastically increased. One of the major areas of concern for many people is the reduction of wrinkles in facial skin. Many different types of facial creams have been developed over the years that claim to reduce wrinkling of the skin, but people have still sought better ways of addressing the problem. One of the newer approaches even includes injecting a form of botulism under the skin to smooth out wrinkles. However, people still seek new products that provide improved results with as little cost, time and pain involved as possible.

There also has been several different devices developed to address the problem of reducing wrinkles in the skin. The following brief descriptions of previously issued United States Patents provide a representation of the devices in the prior art that have been created to address the problem of reducing wrinkles in the skin.

U.S. Pat. No. 4,787,373 issued to Vogel discloses a facial ironer for heating a subject's skin after an emollient has been previously applied. A heating element transfers heat to a soleplate that is manipulated over the skin providing a facial treatment.

U.S. Pat. No. 5,551,949 issued to Kim discloses a heated massage therapy device having a hand-held housing, a mechanical vibration generator disposed within the housing and at least one source of infrared radiation disposed within the housing. The heated massage therapy device provides a thermally efficient and effective means of applying infrared radiation in combination with mechanical vibration to selected portions of a user's anatomy.

U.S. Pat. No. 6,019,482 issued to Everett discloses a hand-held, self contained irradiator powered by batteries. The applicator end provides many diodes that emit electromagnetic radiation in the visible and/or infrared portions of the spectrum. A series of switches are provided so that the user may select which one or ones of the diodes to activate to provide particular wavelengths or colors of radiation to be emitted from the applicator end to be used to treat particular body surface areas for the relief of pain or other problems.

U.S. Pat. No. 6,120,497 issued to Anderson discloses a method for treating wrinkles in skin involving the use of a beam of pulsed, scanned or gated continuous wave laser or incoherent radiation. The method comprises generating a beam of radiation, directing the beam of radiation to a targeted dermal region between 100 microns and 1.2 millimeters below a wrinkle in the skin, and thermally injuring collagen in the targeted dermal region.

U.S. Pat. No. 6,312,397 issued to Gebhard discloses a facial iron comprising a heating element and separate charging base. The facial iron heating element has a spoon shaped heating surface for applying heat to a users skin.

U.S. Pat. No. 6,443,915 issued to Hwang discloses a control method and device of a portable beautifying apparatus. The method and device use galvanic ion current, far infrared ray, and vibration to beautify the human skin.

While some of these devices discussed may provide a certain amount of noticeable results in reduction of wrinkles of the skin, there still remains a need for a non-invasive apparatus that produces improved wrinkle reduction in the skin. To answer this need, the claimed invention provides a method and apparatus for aesthetic skin treatments.

SUMMARY OF THE INVENTION

To satisfy the need for an apparatus that reduces the appearance of wrinkles in the skin, the claimed invention provides a method and apparatus for aesthetic skin treatments. It has been previously known that placing LEDs emitting light of differing wavelengths adjacent the skin of a subject can provide beneficial results to the subject. However, varying the wavelength of the light alone and maintaining other characteristics of the light emitted by the LEDs unchanged produces minimal results. The wavelengths of the LEDs employed in the claimed invention are used as carriers to transfer modulation of the emitting frequency and power output of the LEDs to provide an aesthetic skin treatment to the skin.

A primary object of the claimed invention is to provide a new apparatus for aesthetic skin treatments that provides improved results over previous devices.

Another object of the claimed invention is to provide a new method of aesthetically treating the skin that does not require a medical professional to perform the method.

A further object of the claimed invention is to provide an apparatus that modulates the emitting frequency of an electrical light source during an aesthetic skin treatment.

An even further object of the claimed invention is to provide an apparatus that modulates the power output of an electrical light source during an aesthetic skin treatment.

To accomplish these objects as well as others that will become apparent after reading this specification and viewing the appended drawings, a new method and apparatus for aesthetic skin treatments is provided. The preferred embodiment of the apparatus generally comprises a control console, a large pulsator having a plurality of light emitting diodes (LEDs) and a small pulsator having a single LED. The term pulsator is being used to denote a probe or applicator that conveys pulsated light from the LEDs within the large pulsator and small pulsator.

The control console generally comprises a session timer display with controls, a massage control, a small pulsator control, a pause control, a large pulsator control, a Phase I control, a Phase II control and a Phase III control. The session timer has a two digit LED timer display controlled by two timer select controls that are provided for an operator to set the number of minutes that a particular session will last. The massage control 70 allows an operator to activate a vibration means within the large pulsator to provide a massaging action to the subject's skin when the large pulsator is being used.

The small pulsator has a single 625 nm wavelength LED at 40 mW centrally located at the tip that is powered by a power supply cord removably connected to the control console. The small pulsator is used in applications where the area of skin that is targeted for aesthetic skin treatment is small. The tip of the small pulsator is preferably covered with a sanitary cover.

The large pulsator and vibration means are supplied power by a power supply cord that is removably connected to the control console. The large pulsator has a head with 12 radially spaced 940 nm wavelength LEDs at 20 mW about the head and a 625 nm wavelength LED at 160 mW is located at the center of the head. The large pulsator is used in application where a general area of skin is targeted for aesthetic skin treatment. The head of the large pulsator is preferably covered with a sanitary cover.

The circuitry within the control console provides a frequency modulating means and a power output modulating means that control the emitting frequency and power output of the LEDs within the large pulsator and small pulsator. An operator of the apparatus can choose among three phases where the emitting frequency and power output of the LEDs are varied for different periods of time to achieve certain desired results. The modulation of the emitting frequency and power output of the LEDs provide a pulsating effect that manipulates the skin of a subject being treated.

BRIEF DESCRIPTION OF THE DRAWINGS

FIG. 1 shows a perspective view of the apparatus for aesthetic skin treatments.

FIG. 2 shows a perspective view of the large pulsator and sanitary cover.

FIG. 3 shows a plan view of the head of the large pulsator.

FIG. 4 shows a perspective view of the small pulsator and sanitary cover.

FIG. 5 shows a plan view of the control console of the apparatus.

FIG. 6 shows how the large pulsator is used.

FIG. 7 shows how the small pulsator is used.

FIG. 8 shows a diagram of the control circuitry of the apparatus.

DETAILED DESCRIPTION OF THE PREFERRED EMBODIMENT

Figure 1:
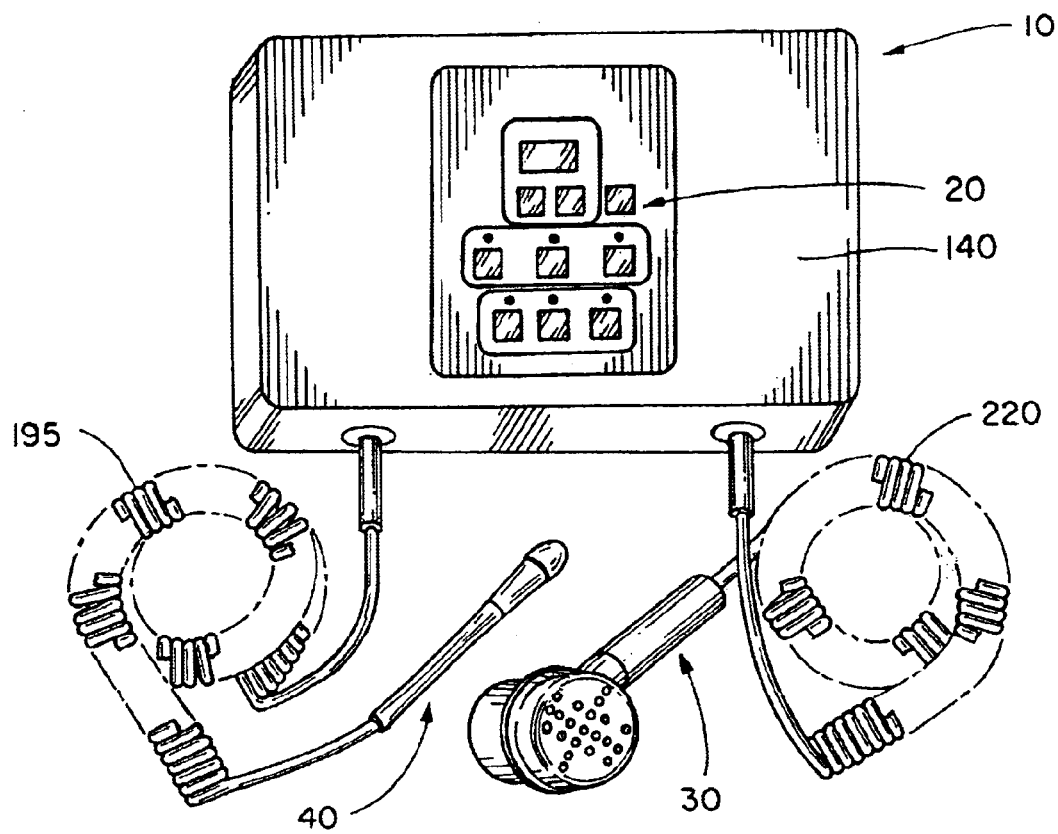
FIG. 1.

Turning now to the drawings, FIG. 1 shows the preferred embodiment of the apparatus 10 for aesthetic skin treatments. The preferred embodiment of the apparatus 10 generally comprises a control console 20, a large pulsator 30 having a plurality of light emitting diodes (LEDs) and a small pulsator 40 having a single LED.

Figure 5:
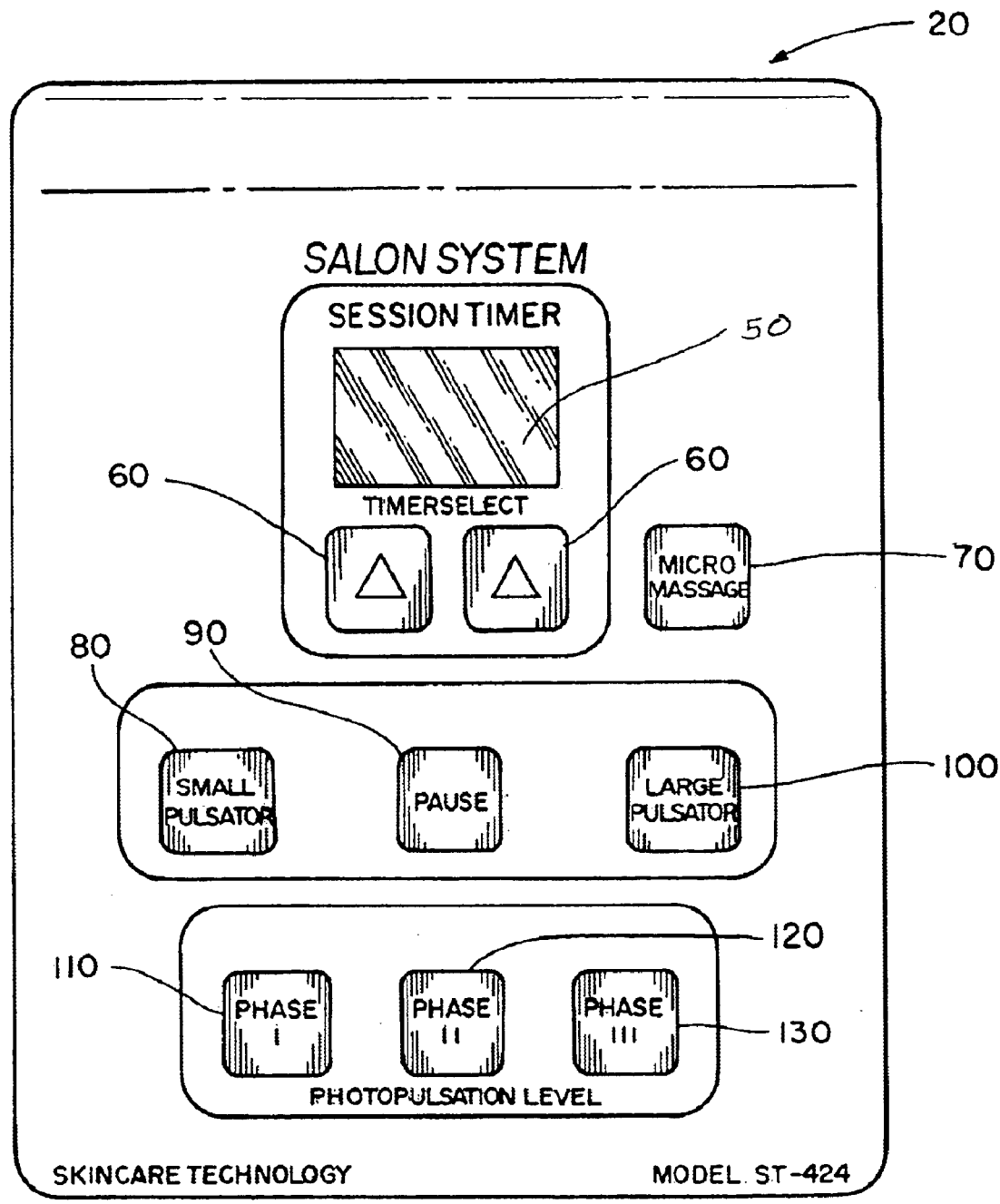
FIG. 5.
Figure 8:
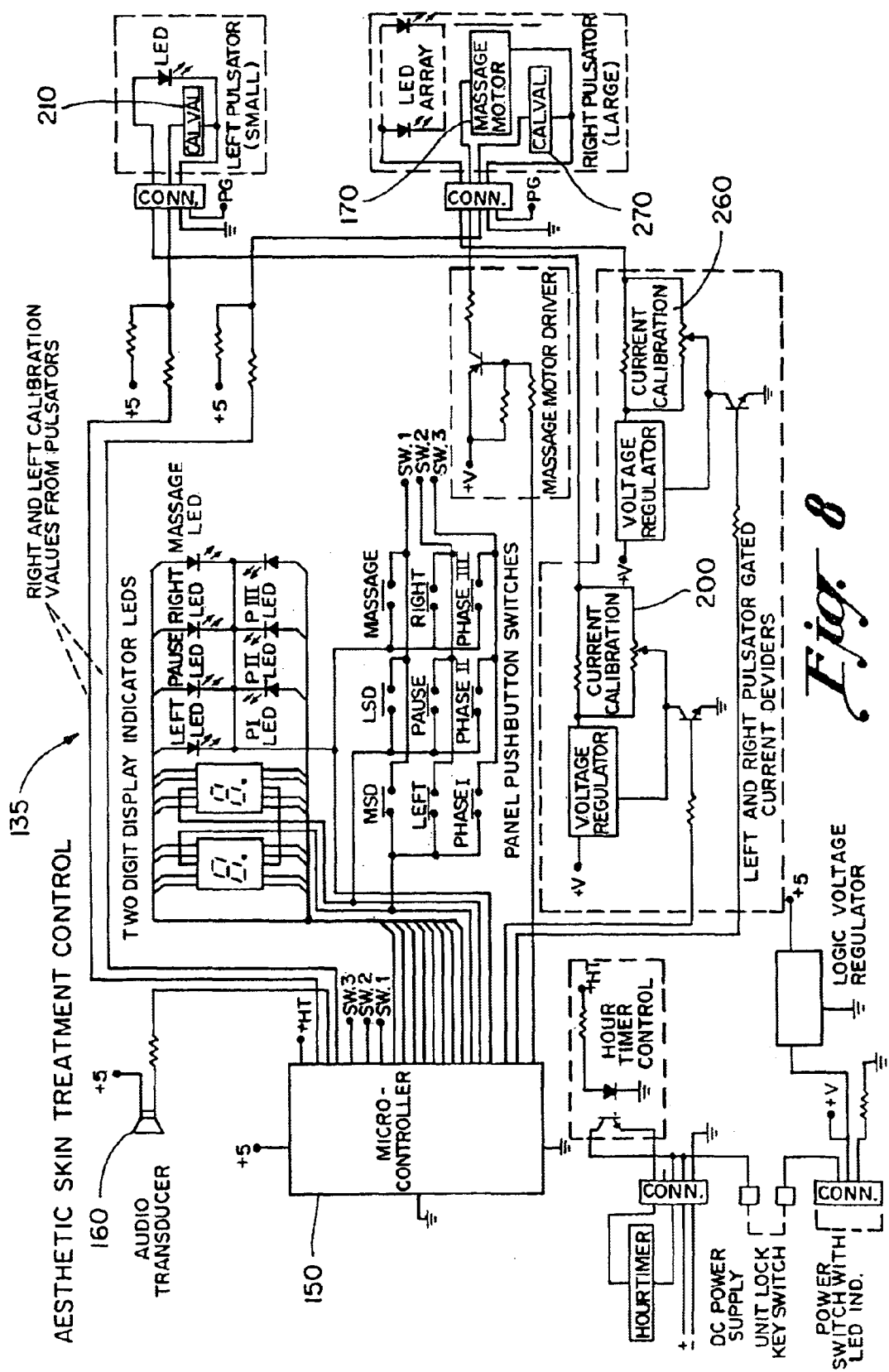
FIG. 8.

FIG. 5 shows that the control console 20 generally comprises a session timer display 50 with controls 60, a massage control 70, a small pulsator control 80, a pause control 90, a large pulsator control 100, a Phase I control 110, a Phase II control 120, a Phase III control 130 and a power switch control (not shown). Each control has an LED adjacent the control that provides a visual indication as to the status of the particular control. The control console 20 may optionally have a unit lock key switch (not shown) to prevent unauthorized use of the apparatus 10. FIG. 8 shows a block diagram of the circuitry 135 that is contained within the control console housing 140 and is controlled by a microcontroller 150. Power is supplied to the circuitry 135 as unregulated 12 volts DC derived from either a battery or from a conventional unregulated AC/DC power supply.

The session timer has a two digit LED timer display 50 controlled by two timer select controls 60 that are provided for an operator to set the number of minutes that a particular session will last. An audible alarm 160 is also provided that can be programmed to notify the operator of a predetermined time interval, signaling that the operator should reposition the pulsator to a different portion of the skin targeted for aesthetic treatment to assist the operator in applying an even aesthetic skin treatment to a subject. Preferably, the audible alarm is programmed to beep every 10 seconds during use of the large pulsator and every 18 seconds during the use of the small pulsator. However, the microcontroller can be programmed to allow an operator of the apparatus 10 to change the audible alarm time intervals to meet particular needs. FIG. 8 shows how the session timer 50 and audible alarm 160 are connected in the circuitry 135 contained within the control console housing 140.

The massage control 70 allows an operator to selectively activate a vibration means 170 within the large pulsator 30 to provide a massaging action to the subject's skin when the large pulsator 30 is being used. FIG. 8 shows how the massage control 70 is connected in the circuitry 135 contained within the control console housing 140 and to the vibration means 170 in the large pulsator 30.

Figure 4:
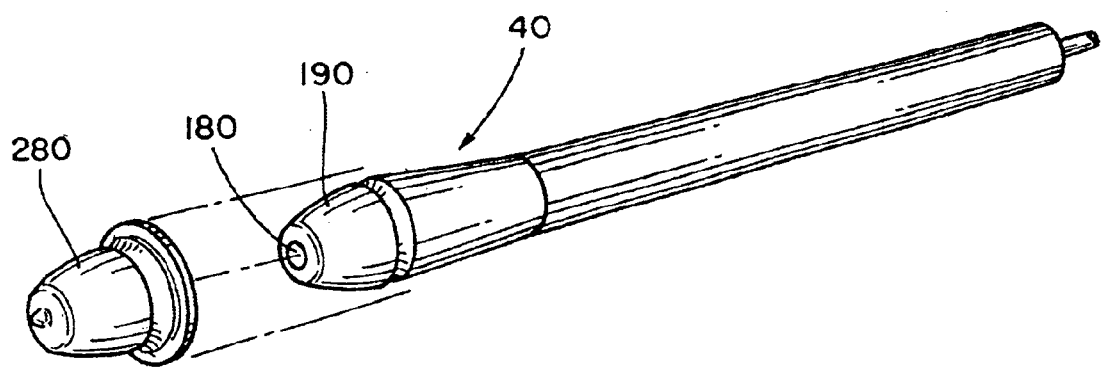
FIG. 4.
Figure 7:
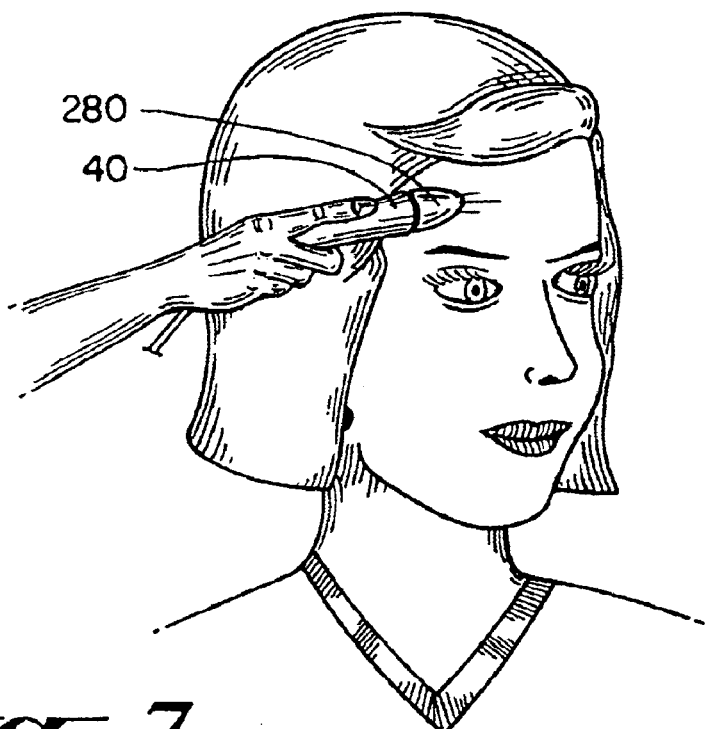
FIG. 7.

The small pulsator 40 shown in FIGS. 4 and 7 is controlled by the small pulsator control 80 that allows an operator to selectively activate the small pulsator 40 for use during a session. The small pulsator 40 has a single 625 nm wavelength LED at 40 mW 180 centrally located at the tip 190 that is powered by a power supply cord 195 removably connected to the control console 20 as shown in FIG. 1. The circuitry 135 within the control console housing 140 provides a calibration driver 200 that works with a calibration resistor 210 within the small pulsator 40 to calibrate the output of the small pulsator 40 to compensate for variation in LEDs used in the small pulsator 40 from unit to unit to ensure consistent operation of the apparatus 10. FIG. 8 shows how the small pulsator 40, small pulsator control 80 and calibration driver 200 are connected in the circuitry 135 contained within the control console housing 140.

The pause control 90 allows an operator to selectively temporarily pause a session, stopping the session timer 50 and turning off the large pulsator 30 and small pulsator 40. FIG. 8 shows how the pause control 90 is connected in the circuitry 135 contained within the control console housing 140.

Figure 2:
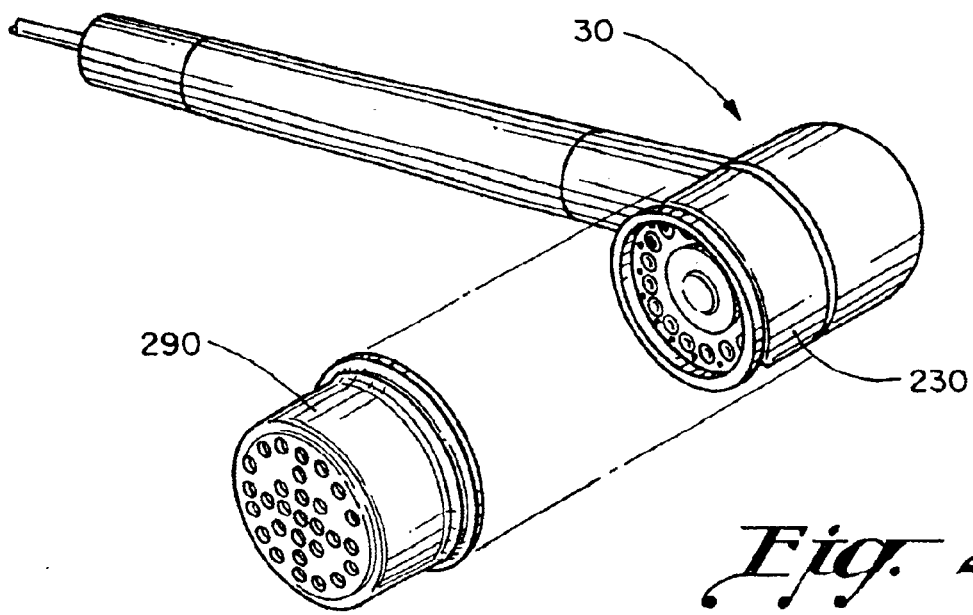
FIG. 2.
Figure 3:
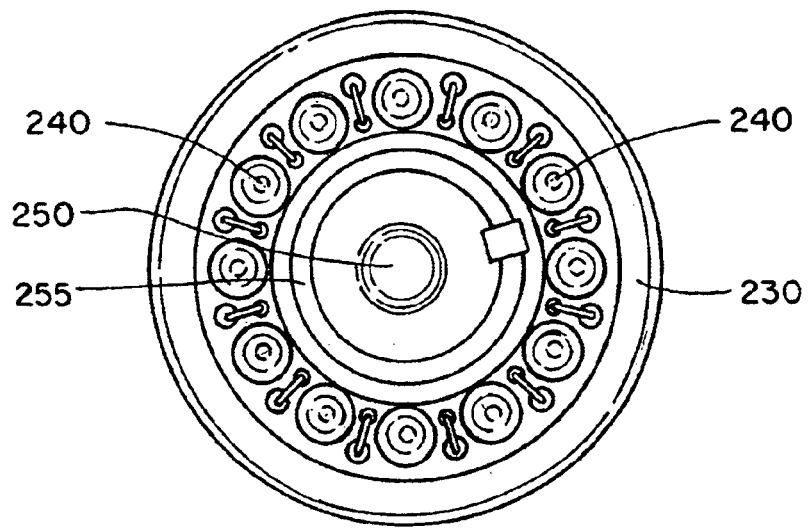
FIG. 3.
Figure 6:
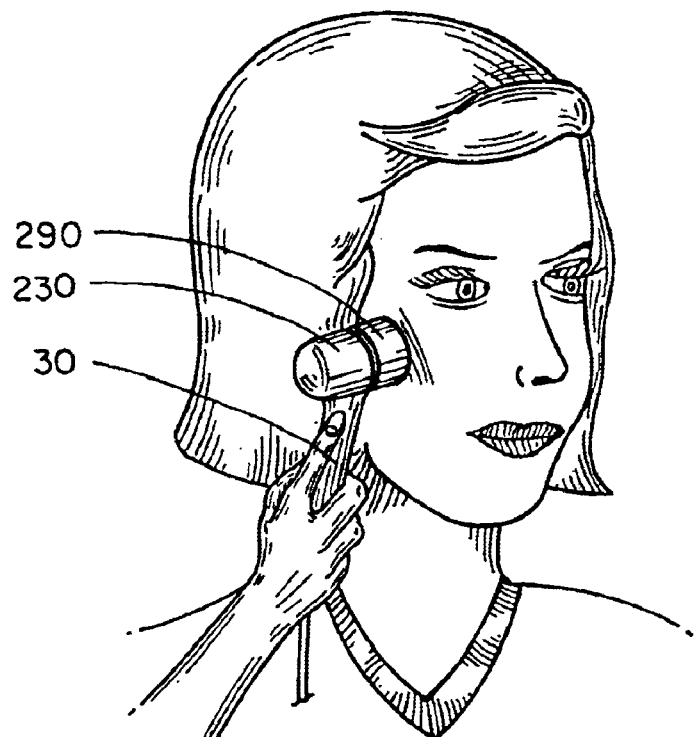
FIG. 6.

The large pulsator 30 shown in FIGS. 2 and 6 is controlled by the large pulsator control 100 that allows an operator to selectively activate the large pulsator 30 for use during a session. The large pulsator 30 and vibration means 170 are supplied power by a power supply cord 220 that is removably connected to the control console 20 as shown in FIG. 1. FIG. 3 shows that the large pulsator 30 has a head 230 with 12 radially spaced 940 nm wavelength LEDs at 20 mW 240 about the head and a 625 nm wavelength LED at 160 mW 250 is located at the center of the head 230. The head is designed as a heat sink to dissipate heat away from the LEDs 240 and 250. The large pulsator 30 employs culminating and diffusing lens 255 with the center LED 250 to direct the light emitted from the center LED 250. The circuitry 135 within the control console housing 140 provides a calibration driver 260 that works with a calibration resistor 270 within the large pulsator 30 to calibrate the output of the large pulsator 30 to compensate for variation in LEDs used in the large pulsator 30 from unit to unit to ensure consistent operation of the apparatus 10. FIG. 8 shows how the large pulsator 30, large pulsator control 100 and calibration driver 260 are connected in the circuitry 135 contained within the control console housing 140.

The circuitry 135 within the control console housing 140 provides a frequency modulating means and a power output modulating means that control the emitting frequency and power output of the LEDs within the large pulsator 30 and small pulsator 40. The Phase controls 110–130 modulate the emitting frequency of the LEDs in the small pulsator 40 and large pulsator 30 for different time intervals at the following frequencies:

| | |
|---|---|
| Phase I | 73 Hertz for 1 second, 292 Hertz for 1 second, and 584 Hertz for one second. |
| Phase II | 73 Hertz for 2 seconds, and 584 Hertz for 1 second. |
| Phase III | 73 Hertz for 4 seconds, and 584 Hertz for 1 second. |

The Phase controls 110–130 also modulate the power output of the LEDs in the large pulsator 30 and small pulsator 40 to the following radiant light levels at the surface of the skin:

| | Large Pulsator | Small Pulsator |
|---|---|---|
| Phase I | 60 mW/cm$^2$ | 6 mW/cm$^2$ |
| Phase II | 70 mW/cm$^2$ | 7 mW/cm$^2$ |
| Phase III | 80 mW/cm$^2$ | 8 mW/cm$^2$ |

The apparatus 10 is used by first switching on the power switch to the apparatus 10. When power is initially provided to the apparatus 10, the microcontroller 150 sets the apparatus 10 to Pause mode, the phase controls to phase I operation, the massage control 70 to off, and resets the session timer 50 to zero minutes. An operator then sets the various controls on the control console 20 to their desired settings in order to complete an aesthetic skin treatment session by first setting the session timer 50 to a desired session time interval. Next, the operator will select the phase control 110–130 desired for the particular session. The Phase controls can be changed at any time during a session by pressing the appropriate control. The associated LED indicator will illuminate reflecting the phase status within the microcontroller 150 with only one of the LED indicators being illuminated at a time. During operation of the apparatus 10, the microcontroller 150 continuously cycles through the emitting frequencies based upon the phase control selection.

The operator then selects the desired pulsator control 80, 100 for the particular session. If the large pulsator 30 is selected for a session, the operator has the option of selecting the massage control 70 to activate the vibration means 170 within the large pulsator 30. When either the large pulsator or the small pulsator is selected, the pause LED will go out indicating that the pause control has been deactivated.

The small pulsator 40 is used as shown in FIG. 7 in applications where the area of skin that is targeted for aesthetic skin treatment is small. The tip 190 of the small pulsator 40 is preferably covered with a sanitary cover 280 as shown in FIGS. 4 and 7 made of translucent plastic that is disposed of after each treatment. The 625 nm wavelength of the LED is used as a carrier to deliver the modulated emitting frequency and power output of the LED created by the frequency modulating means and the power output modulating means. The modulation of the emitting frequency and the power output of the LED works together to produce an aesthetic skin treatment when the small pulsator 40 is placed adjacent a wrinkle in the skin of a subject.

The large pulsator 30 is used as shown in FIG. 6 in applications where a general area of skin is targeted for aesthetic skin treatment. The head 230 of the large pulsator 30 is preferably covered with a sanitary cover 290 as shown in FIGS. 2 and 6 made of translucent plastic that is disposed of after each treatment. The 940 nm wavelength of the radially spaced LEDs and the 625 nm wavelength of the centrally located LED are used as carriers to deliver the modulated emitting frequency an power output of the LEDs created by the frequency modulating means and the power output modulating means. The modulation of the emitting frequency and power output of the LEDs work together to produce an aesthetic skin treatment when the large pulsator 30 is placed adjacent a wrinkle in the skin of a subject.

Although the invention has been described by reference to some embodiments it is not intended that the novel apparatus be limited thereby, but that modifications thereof are intended to be included as falling within the broad scope and spirit of the foregoing disclosure, the following claims and the appended drawings.

We claim:

1. An apparatus for treatment manipulation of the skin, the apparatus comprising:

a power supply;

a large pulsator having a plurality of light emitting diodes connected in circuit with the power supply, the light emitting diodes emitting light having at least two different wavelengths;

a small pulsator having one light emitting diode connected in circuit with the power supply;

a frequency modulating means connected in circuit with the power supply and the light emitting diodes of the large pulsator and the small pulsator, the frequency modulating means modulating the emitting frequency of the light emitting diodes of the large pulsator and small pulsator to a plurality of different frequencies;

a power output modulating means connected in circuit with the power supply and the light emitting diodes of the large pulsator and the small pulsator, the power output modulating means modulating the power output of the light emitting diodes of the large pulsator and small pulsator; and a phase switching means for selecting between a plurality of operating phases connected in circuit with the power supply and the light emitting diodes of the large pulsator and small pulsator, each operating phase operating the frequency modulating means and power output modulating means in a different predetermined manner.

2. The apparatus of claim 1 further comprising calibration means connected in circuit with the light emitting diodes of the large pulsator and small pulsator for calibrating the power output of the light emitting diodes.

3. The apparatus of claim 2 further comprising a vibration means for vibrating the large pulsator and a vibration switching means for selectively activating the vibration means.

4. The apparatus of claim 3 wherein the frequency modulating means modulates the emitting frequency of the light emitting diodes of the large pulsator and small pulsator from a first frequency ranging from about 50 Hz to about 100 Hz to a second frequency ranging from about 550 Hz to about 650 Hz.

5. The apparatus of claim 4 wherein the power output modulating means modulates the power output of the light emitting diodes of the large pulsator from a first power output measured at skin surface with the large pulsator placed adjacent the skin ranging from about 55 mW/cm$^2$ to about 65 mW/cm$^2$ to a second power output ranging from about 65 mW/cm$^2$ to about 75 mW/cm$^2$.

6. The apparatus of claim 5 wherein the power output modulating means modulates the power output of the light emitting diodes of the large pulsator to a third power output ranging from about 75 mW/cm² to about 85 mW/cm².

7. The apparatus of claim 6 wherein each operating phase operates the frequency modulating means and the power output modulating means for varying periods of time.

8. An apparatus for treatment manipulation of the skin, the apparatus comprising:

a housing;

a power supply within the housing;

a large pulsator having a head portion and a power supply cord connected in circuit with the power supply;

a plurality of radially spaced light emitting diodes within the head portion of the large pulsator powered by the power supply through the power supply cord, the light emitting diodes emitting light having at least two different wavelengths;

a small pulsator having a tip portion and a second power supply cord connected in circuit with the power supply;

at least one light emitting diode located within the tip portion of the small pulsator powered by the power supply through the second power supply cord;

frequency modulating means within the housing connected in circuit with the power supply and the light emitting diodes of the large pulsator and the small pulsator, the frequency modulating means modulating the emitting frequency of the light emitting diodes of the large pulsator and small pulsator to a plurality of different frequencies;

power output modulating means within the housing connected in circuit with the power supply and the light emitting diodes of the large pulsator and the small pulsator, the power output modulating means modulating the power output of the light emitting diodes of the large pulsator and small pulsator;

phase switching means within the housing for selecting between a plurality of operating phases connected in circuit with the power supply and the light emitting diodes of the large pulsator and small pulsator, each operating phase operating the frequency modulating means and power output modulating means in a different predetermined manner; and calibration means within the housing connected in circuit with the light emitting diodes of the large pulsator and small pulsator for calibrating the power output of the light emitting diodes.

9. The apparatus of claim 8 further comprising vibration means within the head of the large pulsator for vibrating the large pulsator and vibration switching means within the housing connected in circuit with the power supply for selectively activating the vibration means.

10. The apparatus of claim 8 further comprising a centrally located light emitting diode within the head portion of the large pulsator.

11. The apparatus of claim 10 further comprising a heat sink adjacent the centrally located light emitting diode to dissipate heat away from the centrally located light emitting diode.

12. The apparatus of claim 8 wherein the frequency modulating means modulates the emitting frequency of the light emitting diodes of the large pulsator and small pulsator from a first frequency ranging from about 50 Hz to about 100 Hz to a second frequency ranging from about 550 Hz to about 650 Hz.

13. The apparatus of claim 8 wherein the power output modulating means modulates the power output of the light emitting diodes of the large pulsator from a first power output measured at skin surface with the large pulsator placed adjacent the skin ranging from about 55 mW/cm² to about 65 mW/cm² to a second power output ranging from about 65 mW/cm² to about 75 mW/cm².

14. The apparatus of claim 13 wherein the power output modulating means modulates the power output of the light emitting diodes of the large pulsator to a third power output ranging from about 75 mW/cm² to about 85 mW/cm².

15. The apparatus of claim 14 wherein each operating phase operates the frequency modulating means and the power output modulating means for varying periods of time.

16. The apparatus of claim 8 further comprising a large translucent cover sized and shaped to removably frictionally fit over the head portion of the large pulsator, the large translucent cover contacting skin of a person during use.

17. The apparatus of claim 8 further comprising a small translucent cover sized and shaped to removably frictionally fit over the tip portion of the small pulsator, the small translucent cover contacting skin of a person during use.

* * * * *